United States Patent [19]

Straihammer

[11] 3,963,890

[45] June 15, 1976

[54] FOOT OPERATED SWITCH ASSEMBLY WITH LATCHING STRUCTURE FOR OPERATOR

[75] Inventor: Reinhard Straihammer, Kirschhausen, Germany

[73] Assignee: Siemens Aktiengesellschaft, Erlangen, Germany

[22] Filed: June 19, 1973

[21] Appl. No.: 371,543

[30] Foreign Application Priority Data

June 26, 1972 Germany............................ 2231266

[52] U.S. Cl. ........................... 200/86.5; 200/153 C; 74/512
[51] Int. Cl.² ...................... H01H 3/14; G05G 1/14
[58] Field of Search ........................... 32/22, 23, 28; 200/86.5, 153 C, 61.89; 74/478, 478.5, 512; 338/47, 78, 108, 215, 153; 318/446, 551

[56] References Cited
UNITED STATES PATENTS

| | | | |
|---|---|---|---|
| 543,855 | 8/1895 | Denison | 318/551 X |
| 804,595 | 11/1905 | Garhart | 318/551 |
| 2,671,268 | 3/1954 | Crawford | 200/86.5 X |
| 2,857,493 | 10/1958 | Tascher | 200/86.5 |
| 3,117,200 | 1/1964 | Wolff | 200/86.5 |
| 3,296,698 | 1/1967 | Staunt | 74/478 X |
| 3,471,928 | 10/1969 | Billin | 200/86.5 X |
| 3,502,833 | 3/1970 | Rossini et al. | 200/86.5 |
| 3,742,167 | 6/1973 | Muther | 200/86.5 |

FOREIGN PATENTS OR APPLICATIONS 643,505 4/1937 Germany .......................... 200/86.5

*Primary Examiner*—James R. Scott
*Attorney, Agent, or Firm*—Haseltine, Lake & Waters

[57] ABSTRACT

A foot control installation for drives, particularly for dental drill drives or motors, including a housing and an actuating member projecting therefrom with a foot contact, with the actuating member adapted to be displaced from an initial into an operative position for actuation of a control element for the drive. The installation includes at least two switches selectively actuated through a selector switch so as to provide for different modes of operation through either a first actuating member or another actuating element.

11 Claims, 9 Drawing Figures

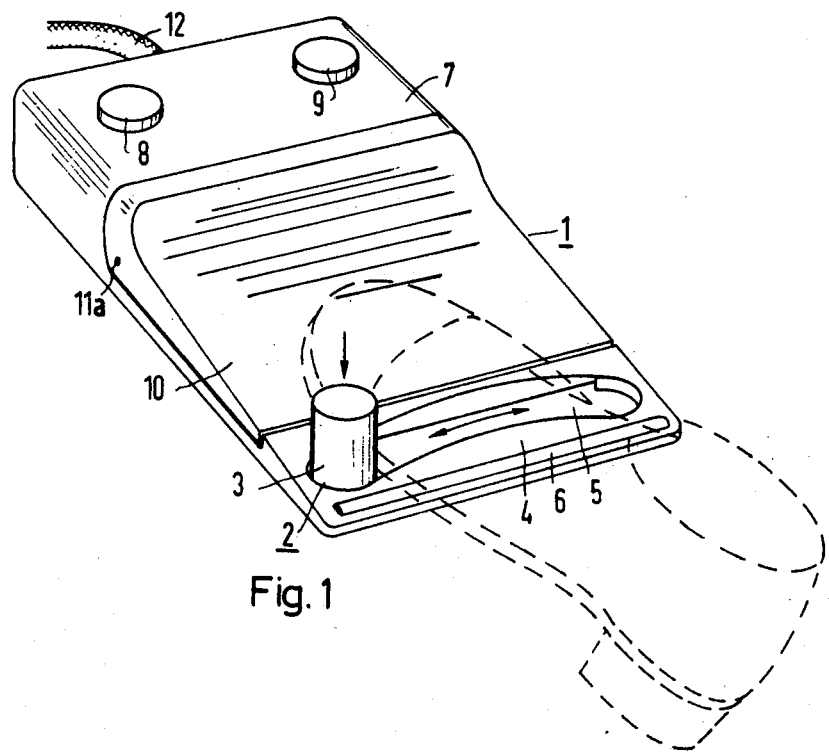
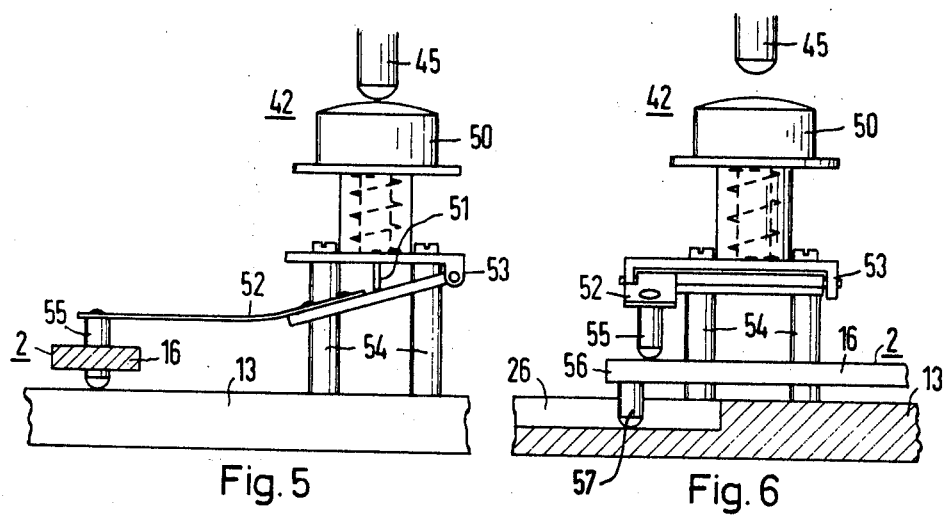

3,963,890

FOOT OPERATED SWITCH ASSEMBLY WITH LATCHING STRUCTURE FOR OPERATOR

FIELD OF THE INVENTION

The present invention relates to a foot control installation for drives, particularly for dental drill drives or motors, including a housing and an actuating member projecting therefrom with a foot contact, with the actuating member adapted to be displaced from an initial into an operative position for actuation of a control element for the drive.

DISCUSSION OF THE PRIOR ART

In known control installations of this type, upon displacement of an actuating member from its initial position, the drive may be actuated and, upon further displacement of the actuating member, its rotational speed continuously varied. In its final position, in effect, the operative end position of the actuating member, the drive rotates at its maximum prescribed speed.

Particularly in the dental technology, the continual rotary speed adjustment of the drive by means of the actuating member is not always desired. Thus, for example, during polishing operations in the laboratory, work must frequently be carried out over extensive periods of time at one and the same, or constant rotational speed. However, with the initially described control installations this operation cannot be satisfactorily effected, since, after each interruption of the operative sequence, upon each renewed actuation of the drive through displacement of the actuating member, the rotational speed must again be raised into the previously employed operative rotational speed.

In view of various operative or work practices or requirements which have been generated in the dental technology, a general or overall control over the rotational speed by means of a foot-actuated member cannot be prescribed. Frequently, for example, a hand control for determining the rotational speed of the drive is preferred in contrast to a foot control. However, in order to satisfy both practices, customers must be offered two differently constructed foot control installations, namely, one which provides for a black-white switching of the drive, and another which provides for the in-and-out switching as well as control over the rotational speed through the foot-actuated member.

SUMMARY OF THE INVENTION

Accordingly, an object of the present invention is to provide a foot control installation pursuant to the previously described type, in which both operative practices are satisfied, and which is able to provide a predetermined selective rotary drive speed, the drive as required to be frequently switched out, and upon being reactuated to afford instant operation at the previously determined speed, and which furthermore incorporates the possibility of continuous operation of the drive.

The foregoing task is inventively solved by the present invention by the provision of a foot control installation which is characterized by two switching means adapted to be selectively actuated by a selector switch for the in-and-out switching of the drive, and in which a first of the switching means is operatively connected with the actuating member so as to be actuated upon displacement of the latter from an initial position thereof, and in which the second switching means contains an actuating element which is in spaced relationship with the first switching means. The actuating element of the second switching means may, in a preferred embodiment, be constructed as a foot pressure or step plate. The pressure or step plate may be located at the upper surface of the housing of the foot control installation in proximity to the operative path of the foot contact defined by the displacement of the actuating member from its initial into its operative end position. The step plate, furthermore, may be formed in a desk-shaped configuration or as a sloped surface which inclines or slopes downwardly towards the foot contact. This permits the relatively simple switching of the switch which is connected with the step plate without requiring any extensive movement of the foot. The distance between the sloped end of the step plate adjacent the foot contact and its tilting axis is relatively large, so as to afford adequate switching movement even at relatively small plate tilting angles. The actuating member is preferably subjected to the action of biasing return means tending to move it into its initial position, and may be arrested in its operative end position by a suitable locking arrangement. The locking arrangement may be constructed in a manner, so as to be releasable upon a reverse pressure being applied against the foot contact. For example, the locking arrangement may comprise a magnetic lock. In another embodiment, the locking arrangement may be provided with a bending spring which has a lock pin so as to, in the operative end position of the actuating member, cause the engagement between the lock pin and the actuating member to thereby arrest the latter, and in which the bending spring is constructed and located so as to be able to release the lock pin from its locking position when pressure is applied to the foot contact in opposition to the arresting effect imparted by the locking arrangement. The locking arrangement and the selector switch may comprise a common actuating element. The actuating element may be formed of a pressure knob adapted to be actuated by downward pressure being exerted thereon by the foot. The pressure knob may also be provided with a pre-selection device for operation of the locking arrangement. This allows for the possibility of effecting arresting of the actuating member at any desired instance, and to thereby deactivate the in-and-out switch which is connected to the actuating member.

BRIEF DESCRIPTION OF THE DRAWINGS

Further advantages may be ascertained as follows in the detailed description of exemplary embodiments of the invention, taken in conjunction with the accompanying drawings, in which:

FIG. 1 illustrates in a perspective view a foot control installation according to the present invention;

FIG. 5 shows a locking arrangement for the actuating element of the foot control installation in a front plan view;

FIG. 6 ilustrates the locking arrangement of FIG. 5 in side elevational view, partly in section;

DETAILED DESCRIPTION

Figure 2:
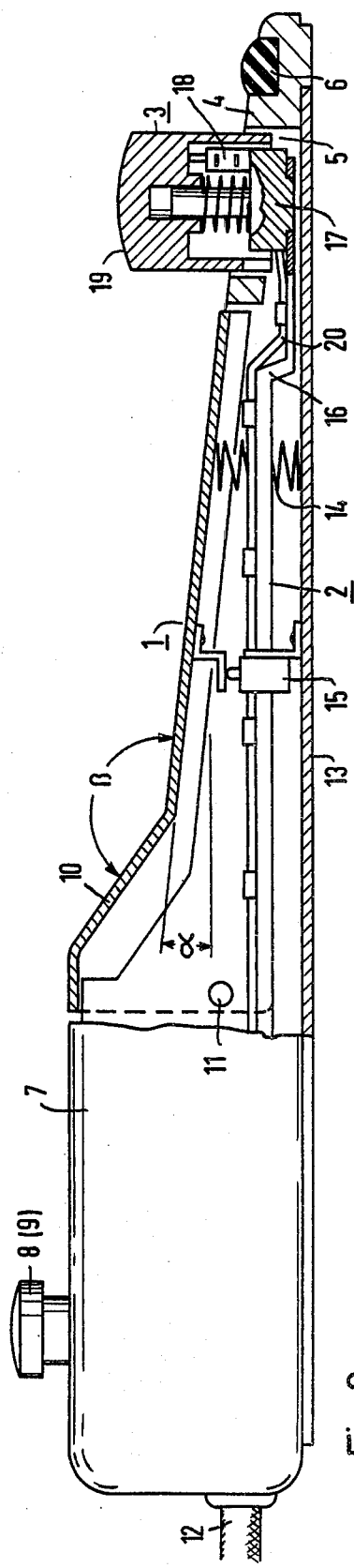
FIG. 2 shows the foot control installation of FIG. 1 in a side view, partly in section.

Referring now in detail to FIG. 1 of the drawings, there is illustrated in a perspective view a foot control installation, as utilized for dental apparatuses, for example, dental drill drives or motors. The foot control installation includes, in plan view, a rectangular housing 1 having an actuating member 2 projecting therefrom, which is adapted to be displaced or actuated by the foot of an operator. The actuating member 2 is provided with a foot contact 3, and may be moved in the directions of the illustrated arrow from an initial position into operative positions. In its initial position, the actuating member (arm 28 in FIG. 3) extends approximately parallel to the two lengthwise sides of the rectangular housing 1. The distance of the initial position with respect to an operative end position of the foot contact (in the Figure, one operative end position is illustrated) defines the path of movement of the actuating element, as well as that of the foot contact. The center or intermediate position of the actuating element between the two operative end positions forms its initial position. In the region of foot contact 3 there is provided a foot step saddle or frame 4 which includes an aperture 5 in the area of the path of movement of the foot contact. The step frame 5 assures that upon manipulation of the actuating element, the control installation does not slide relative to its supported position. The step frame has its lower surface located in the plane of the support surface of the housing 1 which, in this instance, coincides with the bottom surface of a base plate 13 supported on the floor. A plastic material strip or runner 6 having an upwardly curved upper surface is positioned in a recess formed in step frame 4 so as to afford the advantage that upon the operator stepping onto the step frame only a relatively small upper surface portion thereof is subject to a weight or load. Consequently, the foregoing assures that only relatively low frictional forces are produced between the sole of the foot and the plastic material runner 6, while nevertheless the entire weight load may be conducted to the support (floor). The operator can thereby easily manipulate the actuating member with his foot, without the housing being displaced relative to its position on the floor.

In the rear portion 7 of the housing 1 there are positioned, at its upper surface, two actuating elements 8 and 9 which are operatively connected to switching elements located interiorly of housing portion 7. The support for actuating member 2 is also located in housing portion 7. A foot step or pressure plate 10 extends between housing portion 7 and the forward portion of the foot control installation, and is supported so as to be tiltable about an axis 11 by means of a shaft 11a which extends in parallel to the linear path of movement of the actuating member. The step plate 10 is desk-shaped and is sloped upwardly at an angle of $\alpha = 3°$ to $10°$ from the foot contact 3, curving in the final third of its slope upwardly toward an angle $\beta$ of approximately $140°$, and finally joining into the upper surface of housing portion 7. A common inlet conduit is designated by numeral 12, within which the individual electrical conduits leading to the switching and control elements are conveyed into housing 1.

FIG. 2 illustrates the control installation in a side view, in which the forward portion thereof is shown in section. The angle $\alpha$ is designated with respect to the horizontal upper surface of the housing which normally corresponds with the bottom surface of the base plate 13, and the angle $\beta$ with reference to the upper surface of the sloped portion. Upon the operator stepping onto the step plate 10, the latter is tilted about axis 11 in opposition to the biasing force of a spring 14, so as to actuate a switch 15.

As may be ascertained from FIGS. 1 and 2, the step plate 10 extends across the full width of the foot control installation. This renders it possible to provide the desired switching sequence for each operative position of the actuating element 2 by means of a single switch without requiring any large degree of foot motion. The location of the step plate 10 above an arm 16 of the actuating member 2 allows for the connection of the foot contact 3 with a switching member which is actuated by stepping downwardly thereon. This would be rather difficult by positioning a switching bar or runner below arm 16, since this would create the danger that upon axial actuation of the foot contact, the switching runner is concurrently actuated therewith so as to thereby effect an undesired switching sequence. Consequently, the arm 16 of actuating member 2 is provided with an extension 17 which, together with a cap-shaped actuating element 19, forms a switch housing for a switching element 18. A switch supply conduit 20 for the switching element 18 is introduced into extension 17 through a suitable bore, and fastened along arm 16 by means of suitable collars or clamps. The function of both switching elements 15 and 18 is explained in the schematic circuit diagram of FIG. 9.

Figure 3:
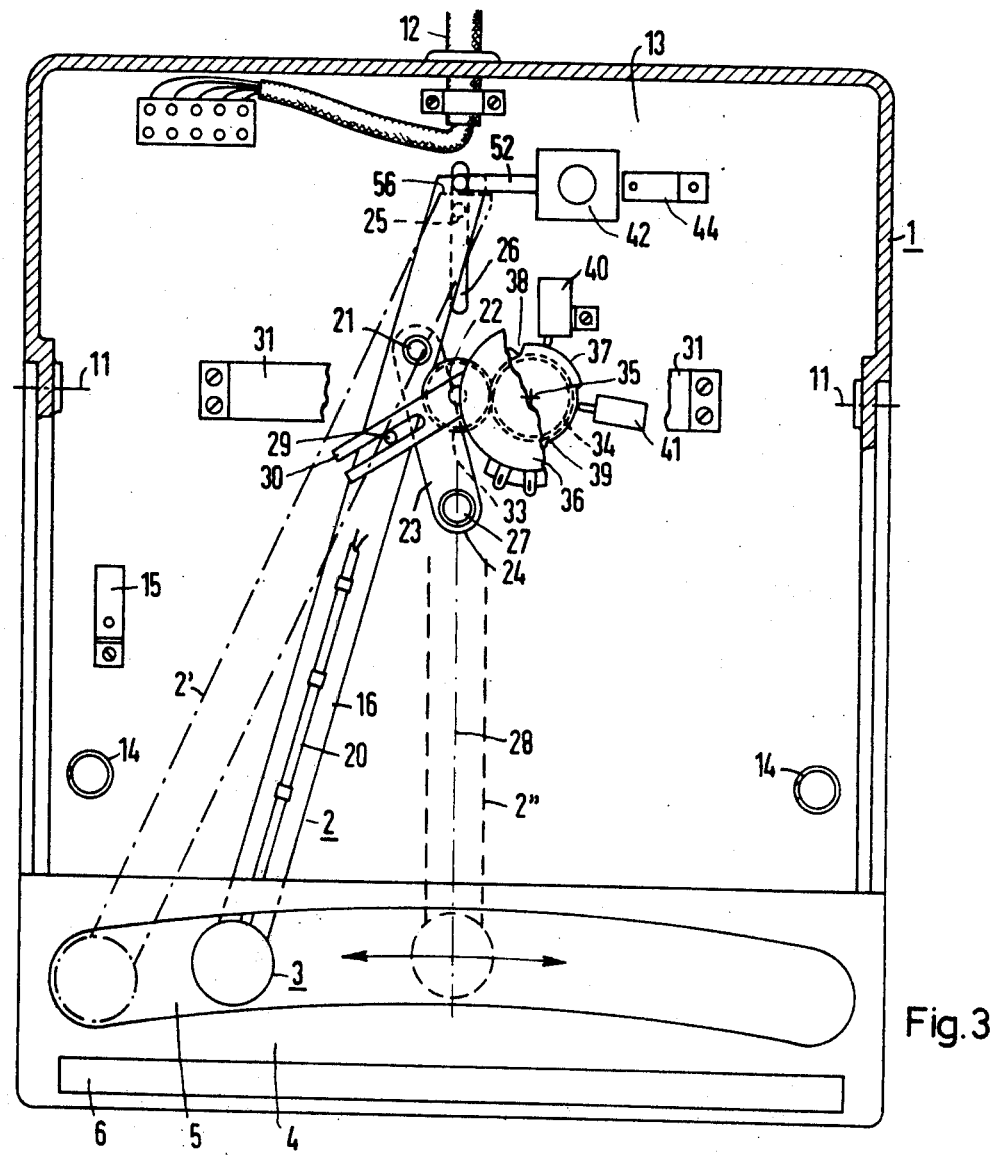
FIG. 3 shows the foot control installation of FIG. 1 in a top plan view without the foot step or pressure plate and housing.

In FIG. 3 there is illustrated, in plan view, a control installation with the housing 1 and step plate 10 not shown for purposes of clarity. The arm 16 of the actuating member 2 is supported at two locations on base plate 13. A first support 21 is located in proximity to foot contact 3, and a second support 25,26 is located remote therefrom. The support 21 is a basically pivotal support and is constructed by the connection of the free end of a stationarily mounted single-arm pivot lever 23 to arm 16. The stationary support is designated by reference numeral 24. The support 25,26 consists of a support projection 25 and a cooperative support which, in effect is a guide path 26 formed in the base plate 13. A support axis 27 for the support 24 coincides with the illustrated center line 28 of the actuating member 2 shown in its initial position. The support 21 is conveyed by means of pivot lever 23, as viewed from the foot contact, along a concavely curved path, while the support projection 25 of the second support, and which is mounted on the actuating member, is conveyed through the linear path of movement so that the support projection 25, upon displacement of the actuating member, is presently moved in the direction of the foot contact in the initial position of the actuating member.

A follower pin 29 which is fastened onto the arm 16 of the actuating member 2 extends into contact with the slot of a fork 30, the latter of which is rotatably journaled on a frame element 31 fastened in base plate 13. A ratchet or gear wheel 33 is mounted on the support axis 32 (FIG. 4) of the fork 30, and engages a gear 34 which in turn is fastened onto the axis 35 of a potentiometer 36. A plate cam 37 having cutout portions 38 and 39 is also supported on the axis 35 of the potentiometer 36. Through plate cam 37 there may be actuated two switching elements 40 and 41 which are adapted to provide a switching sequence described in greater detail in the circuit diagram of FIG. 9.

A locking arrangement 42 is associated with the actuating member 2, by means of which the latter may be arrested in both of its operative end positions to either the left or right of its initial position. In the Figure the left-hand operative end position of the actuating member 2 is illustrated in chain-dotted lines (designated by 2'). In this position the potentiometer 36 is fully effective, in essence, a rotary drive controlled by the potentiometer is operated at its maximum rotational speed. The intermediate or initial position of the actuating member is shown in chain-dot in FIG. 3 of the drawing (designated 2"). The function of the individual switching elements 40, 41 and 44, as well as that of the potentiometer 36, is detailed in connection with the description of the circuit diagram of FIG. 9.

The support of the actuating element 2 in the above illustrated and described manner has the advantage in that the foot contact 3 is conveyed, upon manipulation of the actuating member 2 from its initial position (illustrated by chain-dotted lines 2") in a substantially linear to concavely curved path, as viewed from the foot contact.

This affords the advantage that the foot contact 3, unlike prior art foot control installations, has no motion tending to move away from the foot tip of the operator, but in contrast the foot contact is moved toward the direction of the foot tip. Consequently, this largely eliminates the possibility of slippage occurring between the foot tip of the operator and the foot contact, even during relatively large displacement of the actuating member.

Figure 4:
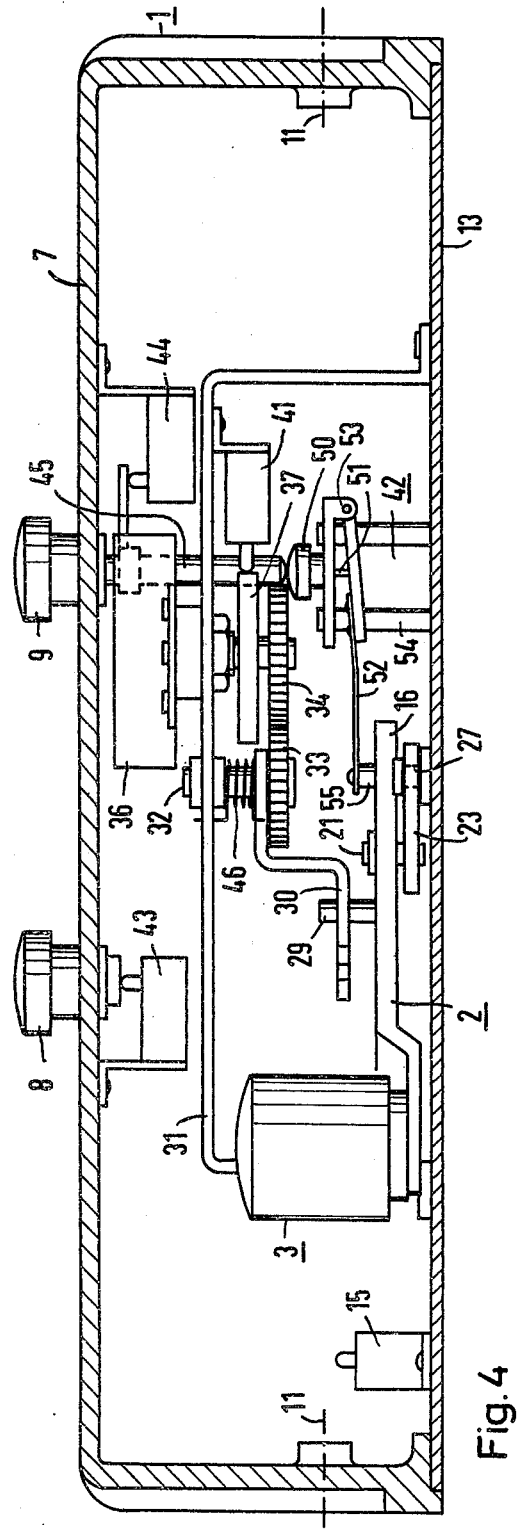
FIG. 4 shows a front elevational view of the foot control installation, with the housing illustrated in section.

The control installation is shown in front view in FIG. 4, in which for illustrative purposes the housing is represented sectioned in a transverse plane. The actuating element 8 is operatively connected with a switch element 43, and the control element 9 with a switch element 44. By means of the last mentioned element, the locking arrangement 42 in FIG. 3 is actuated by means of a contact projection 45 which is connected with actuating element 9. A return spring 46 is mounted on the axis 32 of fork 30, contacting at one end thereof fork 30 and at the other end element 31 whereby the actuating element 2 is always biased thereby from any operative position deviating from its initial position back into its initial position. The functions of switching elements 42 and 44 are explained in further detail in the schematic circuit diagram of FIG. 9.

Details of the locking arrangement are illustrated in FIGS. 5 and 6 of the drawing. In FIG. 5, the locking arrangement is shown in a frontal view, comparably to that of FIG. 4; and in FIG. 6 is shown in a side elevational view. The locking arrangement 42 includes a spring-loaded pressure knob 50 which contains therein a locking mechanism of the type found in the actuating arrangement of a ball writer or pen. With the above mechanism, which is not further described, there is connected a pressure pin 51, which presses onto a leaf spring 52 which is mounted on a retainer 53. The retainer 53 is connected with the base plate 13 by means of support columns 54. The leaf spring 52 includes a pressure pin 55, which in its unlocked positions resiliently contacts the upper surface of arm 16 of the actuating member 2, and in its locked position (locking arrangement) extends behind of the rear edge 56 of arm 16 of the actuating member 2 so as to arrest the latter in that position. In FIG. 5 the locking installation is shown in its locked relationship (also illustrated in chain-dotted lines in FIG. 3), and in FIG. 6 in its unlocked position.

The advantage of the above described locking installations consists of in that the locking sequence may be effected in any desired predetermined position of the actuating member, when the actuating element 9 is downwardly depressed. By means of the mechanism located within the pressure knob 50, the pressure pin 51 is pressed against the leaf spring 52, and consequently the pressure pin 55 is spring-biased against the upper surface of arm 16. When the actuating member 2 reaches its operative end position (left or right) the pressure pin 51 snaps behind the rear edge 56 of arm 16, which has a pin 57 riding in slot 26, and thereby locks the actuating member 2 against any return movement into its initial position. Release or unlocking is effected upon pressure is again applied to the actuating element 9. This causes the release of knob 50, the pressure pin 51 springs upwardly and the leaf spring 52 is, in response to its spring effect, raised above the rear edge of the arm 16, so as to permit the actuating element 2 under the influence of return spring 46 to be returned to its initial position (FIG. 4).

Figure 7:
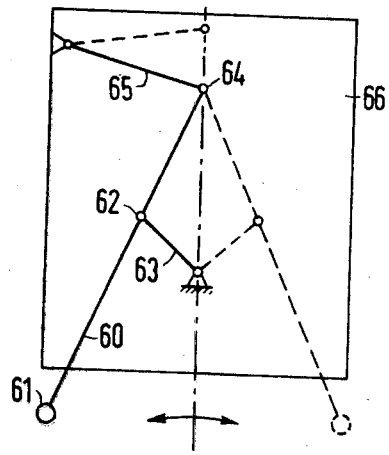
FIG. 7 illustrates schematically the support for the actuating element in a further embodiment thereof.
Figure 8:
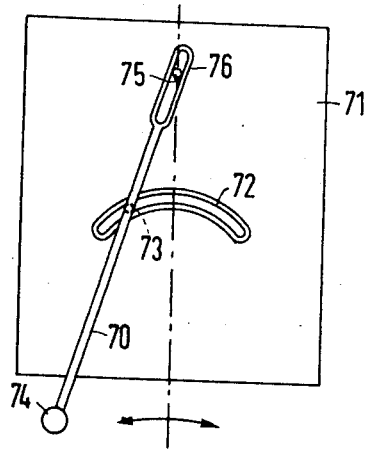
FIG. 8 illustrates schematically a further embodiment of a support for the actuating element.

FIGS. 7 and 8 of the drawing illustrate in a greatly simplified representation further embodiments of the construction and support of the actuating element 2. In the embodiment shown in FIG. 7 of the drawing, an actuating element 60 includes proximate to the foot contact 61 (similar to the embodiment of FIG. 3) a first support 62 which is formed by linkage connection of a rod 63, and a second support 64 which is formed by the connection of a pivot arm 65. The pivot point of the pivot arm 65 on the base plate is determined so that the pivot arm 65 in the initial position of the actuating element 60 (shown in chain-dotted lines) extends approximately at a right angle relative to a connecting line between the second support and the foot contact in the initial position of the actuating element. When the actuating element is symmetrically constructed, this connecting line corresponds to the symmetrical axis of the actuating element. In order to obtain a substantially linear movement for support 64, it is advantageous that the pivot arm 65 be formed as lengthy as possible, whereby the pivot support 64 describes an extremely shallow curved until approximately linear path of movement.

In the embodiment of FIG. 8 of the drawings, an actuating member 70 is guided in a concavely curved guide path 74 located in the base plate 71, as viewed from the foot contact 74. A support portion 73 located on the actuating member may be constituted of a slide bushing or roller. The support 75, 76, which is located remotely from the foot contact 74, is a linear guide. In this connection, the support portion 75 is located on the base plate 71, and the support portion 73 on the actuating member 70.

The advantage of all of the embodiments shown in the figures lies in that, in an extremely simple technological construction there is obtained, as viewed from the foot contact, a concavely curved toward almost a linear path of movement for the foot contact, so as to effectively prevent the actuating element moving away from the foot tip of the operator, when the actuating member is moved from its initial position.

Figure 9:
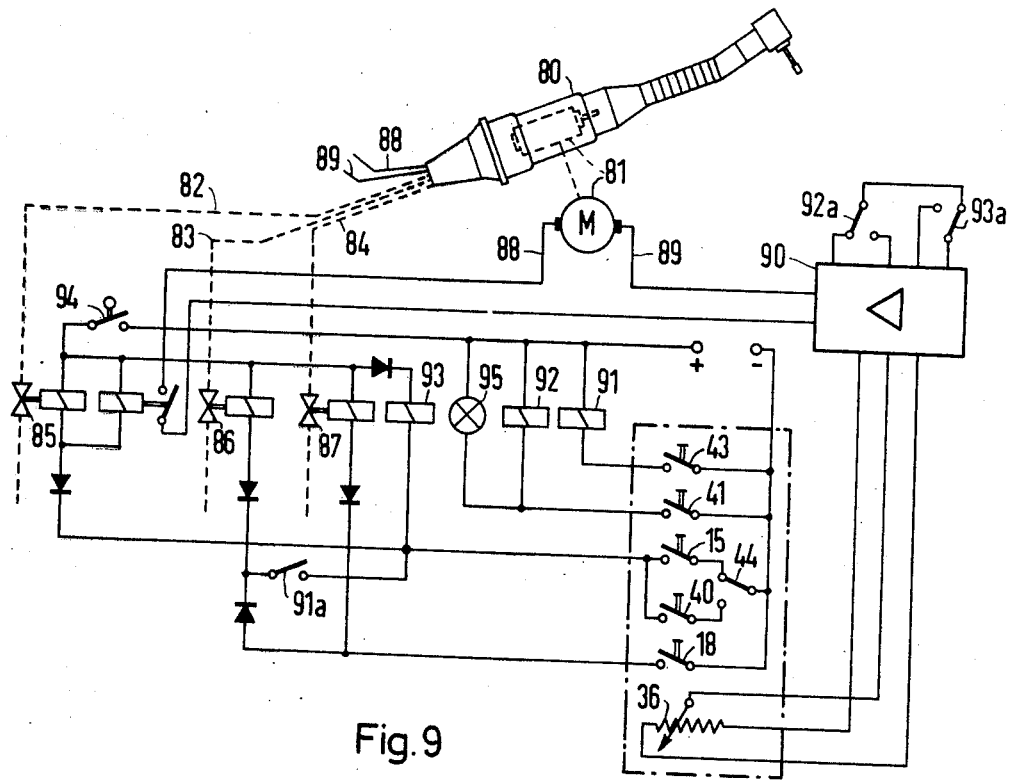
FIG. 9 shows a schematic circuit diagram for another embodiment of the control installation utilized with an electric motor-driven dental hand drill.

In FIG. 9 of the drawing there is illustrated the functional interconnection of the individual control and switching elements with regard to an exemplary embodiment.

Thus, a dental hand drill 80 is driven by an electric motor 81, and includes pressure conduits 82 through 84 for, respectively, the supply of cooling air, spray water and spray air. The control over the foregoing supply is obtained by means of magnetic valves 85, 86 and 87. The electrical inlet conduits for the motor 80 are designated by reference numerals 88 and 89. The conduit 89 extends from the motor into a suitable transformer switch 90 generally utilized for such hand motors, which is adapted to ensure that the rotation of the motor corresponds with that of the variation sensed by potentiometer 36 in response to the displacement of the actuating element. The control installation may further be provided with a switch arrangement for maintaining constant the rotational speed of the motor during any load variations, as well as safety arrangement against overloading of the motor. This type of amplifying or transformer circuit may be constructed in various different manners. The construction thereof has no bearing with respect to the present invention, in view of which the disclosure does not detail any particulars with respect to such switching arrangements.

The switching and control elements contained in the foot control installation are encompassed in chain-dotted representation, and have the from upwardly to downwardly listed following functions. By means of switch 43 (actuated by actuating element 8 shown in FIG. 4) through its switch contact 91a and across relay 91 there is provided for the supply of spray water to the hand drill. The switch 41 (actuated by the plate cam 37 shown in FIG. 3) switches the relay 92 with its switch contacts 92a and reverses the direction of rotation of the motor, inasmuch as both contact poles of the motor are reversed within the amplifying switch 90. By means of switches 15 and 40 (switch 15 is actuated by pressure being imparted to step plate 10, and switch 40 is actuated through plate cam 37) the motor is actuated, in which voltage is conveyed to the motor through relay 93 and corresponding switch contact 93a. A prerequisite is that the switch 94, which is connected with a suitable support arrangement (not shown) for the hand piece, is switched on upon removal of the hand piece from the support arrangement. By means of switch 44 which, in accordance with FIG. 4, is connected with the actuating element 93, there may be provided the option of switching either through pressure or step plate 4 or through actuating member 2, as required. The foot control installation may also be selectively utilized as a mere black-white switch providing for maximum rotational speed (control of the rotational speed may be — if desired — provided from externally of the foot control installation, for example, by a control element in a manually operated grip for the operator), or utilized for the switching including a control function over the actuating member. In the last instance, the rotational speed may be continuously applied. The selective switching is effected from one to the other switching and control modes by imparting pressure to the actuating element 9 through which there is concurrently operated the locking installation for the actuating element 2 as well as the selector switch 44. As can be ascertained from the circuit diagram, upon switching over from the minus pole of the voltage source, the current circuit across switch 40 is opened, and contrastingly the current circuit between the minus pole and the switch 15 is closed. This signifies, that, upon displacement of the actuating member 2 from its initial position, the in-out switch 40 remains ineffective, and the motor cannot be actuated through this switch but only by means of the step plate 10. The direction of the rotation of the motor is automatically obtained through the cam control (shown in FIG. 3). If, for example, the actuating member 2 is moved toward the left from its initial position 2'', the switching pin of the switch 41 is actuated, in view of which through contacts 92a the direction of rotation is determined to be towards the left. Correspondingly, this also applies for the clockwise rotational direction of the motor. Both switches 40 and 41 are so positioned relative to the plate cam, and the plate cam is so constructed, that upon movement of the actuating member from its initial position, the switch 41 is actuated prior to the switch 40, whereby at first the direction of rotation of the motor is determined, and only then is the motor actuated. Reference numeral 18 designates the switch, referred to and described with reference to FIG. 2, which is actuated by depressing the actuating elements 19 of the foot contact 3. By means of this switch, spray air is supplied for short periods of time to the hand drill through magnetic valve 87 (so-called chip-blower effect).

An indicator lamp is designated by reference numeral 95, in view of which the selected and effected direction of motor rotation, for example, the principally used rotational direction, is optically indicated.

It is also noted that the foot control installation may be constructed so as to be displaceable from one side only of an initial position. In this type of construction the need for determining the direction of rotation of the motor by means of the foot-controlled actuating element is obviated.

The utilization of the foot control installation is, of course, not limited to dental drill drives and the aforedescribed exemplary embodiments of rotary drill drives or motors. More frequently, the foot control installation may be employed in any type of apparatus in which a predetermined drive condition must be controlled by foot. Consequently, it is conceivable that the control installation may be utilized to provide control over the output or frequency of an oscillator for a tooth filling removal apparatus, or for the control of the operation of an aspirating apparatus. Furthermore, applications in areas other than medical or dental uses are possible, for example, in the control of the rotational speed of electrically driven sewing machines, or the like.

While there has been shown what is considered to be the preferred embodiment of the invention, it will be obvious that modifications may be made which come within the scope of the disclosure of the specification.

What is claimed is:

1. A foot control installation for drives and the like, comprising a housing; actuating means supported in said housing and having an end portion projecting therefrom, said actuating means being movable between an initial inoperative position and at least one operative position; foot contact means being mounted on the projecting portion of said actuating means; a control element for said drive being operatively connected to said actuating means; first and second switching means for effecting the in-and-out switching of said drive; a selector switch for selectively connecting said switching means to said actuating means; said first switching means being operatively connected with said actuating means so as to be actuated upon displacement of the latter from its initial position, and said second switching means including an actuating element in spaced relationship with said first switching means and actuated through foot pressure, said actuating element for said second switching means including a foot pressure plate articulatedly fastened to said housing and positioned at the upper surface thereof, said pressure plate, as viewed from the foot contact means, extending towards the opposite end of said housing, said pressure plate being located proximate the path of movement of said foot contact means defined by the displacement of said actuating means from its initial position into its operative end positions, means in said housing for biasing said actuating means into its initial position; and a locking arrangement in said housing for arresting said actuating means in its operative end position upon pressure being exerted on said foot contact means.

2. A control installation as claimed in claim 1, said pressure plate being generally desk-shaped and sloped, the sloped surface thereof extending downwardly toward said foot contact means.

3. A control installation as claimed in claim 1, said locking arrangement being releasable upon reverse pressure being applied to said foot contact means.

4. A control installation as claimed in claim 3, said locking arrangement comprising bending spring means including a lock pin, said lock pin adapted to engage said actuating means in locking relationship in the operative end position of the latter, said bending spring means being shaped and located so as to effect release of the lock pin from said actuating means upon reverse pressure being applied to said foot contact means in opposition to the locking effect of said locking arrangement.

5. A control installation as claimed in claim 1, said locking arrangement comprising a magnetic lock.

6. A control installation as claimed in claim 1, comprising a further actuating element connected to said locking arrangement and to said selector switch for common actuation thereof.

7. A control installation as claimed in claim 6, said further actuating element comprising a pressure knob mounted thereon and being actuatable responsive to downwardly-exerted foot pressure.

8. A control installation as claimed in claim 7, said pressure knob comprising a preselection means for selectively effecting operation of said locking arrangement.

9. A control installation as claimed in claim 1, comprising means supporting said pressure plate on said housing for tilting about a horizontal axis extending in proximity to the bottom support surface of said housing.

10. A control installation as claimed in claim 9, the end portion of the sloped surface of said pressure plate proximate to said foot contact means being relatively remotely located from said tilting axis.

11. A control installation as claimed in claim 10, said pressure plate being positioned proximate to the support surface and extending parallel relative thereto.

* * * * *